(12) United States Patent
Gilbeau et al.

(10) Patent No.: US 8,314,205 B2
(45) Date of Patent: Nov. 20, 2012

(54) GLYCEROL-BASED PRODUCT, PROCESS FOR OBTAINING SAME AND USE THEREOF IN THE MANUFACTURING OF DICHLOROPROPANOL

(75) Inventors: Patrick Gilbeau, Braine-Le-Comte (BE); Dominique Balthasart, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 200 days.

(21) Appl. No.: 12/745,802

(22) PCT Filed: Dec. 16, 2008

(86) PCT No.: PCT/EP2008/067624
§ 371 (c)(1),
(2), (4) Date: Aug. 17, 2010

(87) PCT Pub. No.: WO2009/077528
PCT Pub. Date: Jun. 25, 2009

(65) Prior Publication Data
US 2010/0311942 A1    Dec. 9, 2010

(30) Foreign Application Priority Data
Dec. 17, 2007   (FR) .................................. 07 59891

(51) Int. Cl.
*C08G 65/34* (2006.01)
*C08G 73/00* (2006.01)
*C08F 6/00* (2006.01)
*C08J 3/00* (2006.01)

(52) U.S. Cl. ........ 528/425; 528/422; 528/495; 528/501; 528/502 R; 528/502 C (58) Field of Classification Search .................. 528/425, 528/422, 495, 501, 502 R, 502 C
See application file for complete search history.

(56) References Cited

U.S. PATENT DOCUMENTS

| | | |
|---|---|---|
| 280,893 A | 7/1883 | Baujard |
| 865,727 A | 9/1907 | Quenneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |

(Continued)

FOREIGN PATENT DOCUMENTS
BE    422877 A    8/1937

(Continued)

OTHER PUBLICATIONS

Herman A. Bruson, et al., "Thermal Decomposition of Glyceryl Carbonates," Journal of the American Chemical Society, vol. 74, Apr. 1952 pp. 2100-2101.

(Continued)

*Primary Examiner* — Duc Truong
(74) *Attorney, Agent, or Firm* — Oblon, Spivak, McClelland, Maier & Neustadt, L.L.P.

(57) ABSTRACT

The invention relates to a glycerol-based product comprising at least one nitrogen-containing compound and of which the total content of nitrogen-containing compound expressed as elemental nitrogen (N) is less than or equal to 1 g of nitrogen (N)/kg of product, to a process for obtaining glycerol, and to its use in the manufacture of dichloropropanol and of derived products such as epichlorohydrin and products derived from epichlorohydrin.

20 Claims, 1 Drawing Sheet

U.S. PATENT DOCUMENTS

| | | | |
|---|---|---|---|
| 2,505,735 A | 4/1950 | Halbedel |
| 2,726,072 A | 12/1955 | Herman |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,052,612 A | 9/1962 | Henegar et al. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,240,885 A | 12/1980 | Suciu et al. |
| 4,255,470 A | 3/1981 | Cohen et al. |
| 4,294,776 A | 10/1981 | Hardy et al. |
| 4,390,680 A | 6/1983 | Nelson |
| 4,405,465 A | 9/1983 | Moore et al. |
| 4,415,460 A | 11/1983 | Suciu et al. |
| 4,464,517 A | 8/1984 | Makino et al. |
| 4,499,255 A | 2/1985 | Wang et al. |
| 4,595,469 A | 6/1986 | Foller |
| 4,609,751 A | 9/1986 | Hajjar |
| 4,634,784 A | 1/1987 | Nagato et al. |
| 4,655,879 A | 4/1987 | Brockmann et al. |
| 4,935,220 A | 6/1990 | Schneider et al. |
| 4,960,953 A | 10/1990 | Jakobson et al. |
| 4,973,763 A | 11/1990 | Jakobson et al. |
| 4,990,695 A | 2/1991 | Buenemann et al. |
| 5,041,688 A | 8/1991 | Jakobson et al. |
| 5,200,163 A | 4/1993 | Henkelmann et al. |
| 5,278,260 A | 1/1994 | Schaffner et al. |
| 5,286,354 A | 2/1994 | Bard et al. |
| 5,344,945 A | 9/1994 | Grunchard |
| 5,359,094 A | 10/1994 | Teles et al. |
| 5,393,428 A | 2/1995 | Dilla et al. |
| 5,445,741 A | 8/1995 | Dilla et al. |
| 5,478,472 A | 12/1995 | Dilla et al. |
| 5,486,627 A | 1/1996 | Quarderer et al. |
| 5,567,359 A | 10/1996 | Cassidy et al. |
| 5,578,740 A | 11/1996 | Au et al. |
| 5,679,839 A | 10/1997 | Armand et al. |
| 5,710,350 A | 1/1998 | Jeromin et al. |
| 5,731,476 A | 3/1998 | Shawl et al. |
| 5,744,655 A | 4/1998 | Thomas et al. |
| 5,779,915 A | 7/1998 | Becker et al. |
| 5,908,946 A | 6/1999 | Stern et al. |
| 5,993,974 A | 11/1999 | Fukushima et al. |
| 6,024,829 A | 2/2000 | Easter et al. |
| 6,103,092 A | 8/2000 | Silva |
| 6,111,153 A | 8/2000 | Crow et al. |
| 6,142,458 A | 11/2000 | Howk |
| 6,177,599 B1 | 1/2001 | Cowfer et al. |
| 6,270,682 B1 | 8/2001 | Santen et al. |
| 6,288,248 B1 | 9/2001 | Strebelle et al. |
| 6,288,287 B2 | 9/2001 | Ueoka et al. |
| 6,350,888 B1 | 2/2002 | Strebelle et al. |
| 6,350,922 B1 | 2/2002 | Vosejpka et al. |
| 6,521,794 B2 | 2/2003 | Hirota |
| 6,719,957 B2 | 4/2004 | Brady, Jr. et al. |
| 6,740,633 B2 | 5/2004 | Norenberg et al. |
| 6,831,201 B2 | 12/2004 | Katsuura et al. |
| 7,126,032 B1 | 10/2006 | Aiken |
| 7,128,890 B2 | 10/2006 | Ollivier |
| 7,557,253 B2 | 7/2009 | Gilbeau |
| 7,584,629 B2 | 9/2009 | Sohn et al. |
| 7,615,670 B2 | 11/2009 | Gilbeau |
| 2001/0014763 A1 | 8/2001 | Ueoka et al. |
| 2003/0209490 A1 | 11/2003 | Camp et al. |
| 2004/0016411 A1 | 1/2004 | Joyce et al. |
| 2004/0024244 A1 | 2/2004 | Walsdorff et al. |
| 2004/0047781 A1 | 3/2004 | Becenel |
| 2004/0150123 A1 | 8/2004 | Strofer et al. |
| 2004/0179987 A1 | 9/2004 | Oku et al. |
| 2004/0232007 A1 | 11/2004 | Carson et al. |
| 2005/0115901 A1 | 6/2005 | Heuser et al. |
| 2005/0261509 A1 | 11/2005 | Delfort et al. |
| 2006/0052272 A1 | 3/2006 | Meli et al. |
| 2006/0079433 A1 | 4/2006 | Hecht et al. |
| 2006/0123842 A1 | 6/2006 | Sohn et al. |
| 2007/0112224 A1 | 5/2007 | Krafft et al. |
| 2007/0293707 A1 | 12/2007 | Wolfert et al. |
| 2008/0053836 A1 | 3/2008 | Bulan et al. |
| 2008/0146753 A1 | 6/2008 | Woike et al. |
| 2008/0154050 A1 | 6/2008 | Gilbeau |
| 2008/0161613 A1 | 7/2008 | Krafft et al. |
| 2008/0194847 A1 | 8/2008 | Krafft et al. |
| 2008/0194849 A1 | 8/2008 | Krafft et al. |
| 2008/0194851 A1 | 8/2008 | Gilbeau |
| 2008/0200642 A1 | 8/2008 | Krafft |
| 2008/0200701 A1 | 8/2008 | Krafft et al. |
| 2008/0207930 A1 | 8/2008 | Gilbeau et al. |
| 2008/0214848 A1 | 9/2008 | Krafft et al. |
| 2008/0281132 A1 | 11/2008 | Krafft et al. |
| 2009/0022653 A1 | 1/2009 | Strebelle et al. |
| 2009/0131631 A1 | 5/2009 | Krafft et al. |
| 2009/0173636 A1 | 7/2009 | Ooms et al. |
| 2009/0198041 A1 | 8/2009 | Krafft et al. |
| 2009/0270588 A1 | 10/2009 | Krafft et al. |
| 2009/0275726 A1 | 11/2009 | Krafft et al. |
| 2010/0029959 A1 | 2/2010 | Fan et al. |
| 2010/0032617 A1 | 2/2010 | Gilbeau et al. |
| 2010/0105862 A1 | 4/2010 | Krafft et al. |
| 2010/0105964 A1 | 4/2010 | Krafft et al. |
| 2010/0168379 A1 | 7/2010 | Krafft et al. |
| 2010/0170805 A1 | 7/2010 | Krafft et al. |
| 2010/0179300 A1 | 7/2010 | Boulos et al. |
| 2010/0179302 A1 | 7/2010 | Krafft et al. |
| 2010/0212540 A1 | 8/2010 | Bobet et al. |
| 2010/0294727 A1 | 11/2010 | Gilbeau et al. |
| 2010/0305367 A1 | 12/2010 | Borremans |
| 2011/0028683 A1 | 2/2011 | Gilbeau et al. |
| 2011/0152545 A1 | 6/2011 | Balthasart et al. |
| 2011/0166369 A1 | 7/2011 | Krafft et al. |
| 2011/0237773 A1 | 9/2011 | Gilbeau |

FOREIGN PATENT DOCUMENTS

| | | |
|---|---|---|
| CN | 1296003 A | 5/2001 |
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |

| | | | | | | |
|---|---|---|---|---|---|---|
| DE | 3721003 C1 | 12/1988 | | GB | 2336584 A | 10/1999 |
| DE | 43 02 306 | 8/1994 | | HU | 2002-003023 | 3/2004 |
| DE | 4335311 A1 | 4/1995 | | JP | 3927230 B2 | 11/1939 |
| DE | 10203914 C1 | 10/2003 | | JP | 50-062909 | 5/1975 |
| DE | 10254709 A1 | 6/2004 | | JP | 51021635 B | 7/1976 |
| EP | 0 296 341 | 12/1988 | | JP | 55041858 A | 3/1980 |
| EP | 0347618 A2 | 12/1989 | | JP | 5629572 | 3/1981 |
| EP | 0358255 A1 | 3/1990 | | JP | 5699432 | 8/1981 |
| EP | 0421379 A1 | 4/1991 | | JP | 61 112066 A | 5/1986 |
| EP | 0 452 265 | 10/1991 | | JP | 61236749 A | 10/1986 |
| EP | 0518765 A1 | 12/1992 | | JP | 62242638 A | 10/1987 |
| EP | 0522382 A1 | 1/1993 | | JP | 63195288 A | 8/1988 |
| EP | 0535949 B1 | 4/1993 | | JP | 2-137704 | 5/1990 |
| EP | 0561441 A1 | 9/1993 | | JP | 03014527 A | 1/1991 |
| EP | 0563720 A1 | 10/1993 | | JP | 3223267 A | 10/1991 |
| EP | 0568389 A1 | 11/1993 | | JP | 03223267 A | 10/1991 |
| EP | 0582201 A2 | 2/1994 | | JP | 04089440 A | 3/1992 |
| EP | 0 618 170 | 10/1994 | | JP | 04-217637 | 8/1992 |
| EP | 0 916 624 | 5/1999 | | JP | 625196 B2 | 4/1994 |
| EP | 0919551 A1 | 6/1999 | | JP | 06184024 A | 7/1994 |
| EP | 0 774 450 | 2/2000 | | JP | 6321852 A | 11/1994 |
| EP | 1059278 A2 | 12/2000 | | JP | 859593 | 3/1996 |
| EP | 1106237 A1 | 6/2001 | | JP | 09-2999953 | 11/1997 |
| EP | 1153887 A2 | 11/2001 | | JP | 10139700 A | 5/1998 |
| EP | 1163946 A1 | 12/2001 | | JP | 10218810 A | 8/1998 |
| EP | 1231189 A1 | 8/2002 | | JP | 1998218810 A | 8/1998 |
| EP | 1298154 A1 | 4/2003 | | JP | 20000344692 A | 12/2000 |
| EP | 1411027 A1 | 4/2004 | | JP | 2001-037469 | 2/2001 |
| EP | 1752435 A1 | 2/2007 | | JP | 2001-213827 A | 8/2001 |
| EP | 1752436 A1 | 2/2007 | | JP | 2001-261308 | 9/2001 |
| EP | 1760060 A1 | 3/2007 | | JP | 2001-1261581 A | 9/2001 |
| EP | 1762556 A1 | 3/2007 | | JP | 2002-02033 A2 | 1/2002 |
| EP | 1770081 A1 | 4/2007 | | JP | 20020038195 A | 2/2002 |
| EP | 1772446 A1 | 4/2007 | | JP | 20020265986 A | 9/2002 |
| EP | 1775278 A1 | 4/2007 | | JP | 2002-363153 A | 12/2002 |
| EP | 2085364 | 8/2009 | | JP | 2003-89680 A | 3/2003 |
| FR | 1 306 231 | 10/1961 | | JP | 2003081891 A | 3/2003 |
| FR | 1 417 388 | 10/1964 | | JP | 2005007841 A2 | 1/2005 |
| FR | 1 577 792 | 8/1965 | | JP | 2005097177 A2 | 4/2005 |
| FR | 1476073 A | 4/1967 | | JP | 2007-008898 | 1/2007 |
| FR | 2151107 | 4/1973 | | JP | 2009-263338 | 11/2009 |
| FR | 2180138 | 5/1973 | | KR | 900006513 | 11/1987 |
| FR | 2 217 372 | 2/1974 | | KR | 1019920003099 B1 | 4/1992 |
| FR | 2565229 A1 | 12/1985 | | KR | 10-514819 B1 | 9/2005 |
| FR | 2752242 A1 | 2/1998 | | PL | 136598 | 3/1986 |
| FR | 2862644 A1 | 5/2005 | | PL | 162910 | 1/1994 |
| FR | 2868419 A1 | 10/2005 | | SU | 123153 | 1/1959 |
| FR | 2869612 A1 | 11/2005 | | SU | 1125226 | 11/1984 |
| FR | 2869613 A1 | 11/2005 | | SU | 1159716 | 6/1985 |
| FR | 2872504 A1 | 1/2006 | | SU | 1685969 | 10/1991 |
| FR | 2881732 A1 | 8/2006 | | WO | WO 95/14639 | 6/1995 |
| FR | 2885903 A1 | 11/2006 | | WO | WO 96/07617 | 3/1996 |
| FR | 2 912 743 | 8/2008 | | WO | WO 96/15980 | 5/1996 |
| FR | 2913683 | 9/2008 | | WO | WO 97/48667 | 12/1997 |
| FR | 2913683 A1 | 9/2008 | | WO | WO 98/37024 | 8/1998 |
| FR | 2 917 411 | 12/2008 | | WO | WO 99/14208 | 3/1999 |
| FR | 2918058 A1 | 1/2009 | | WO | WO 9932397 A1 | 7/1999 |
| FR | 2925045 A1 | 6/2009 | | WO | WO 0024674 A1 | 5/2000 |
| FR | 2929611 A1 | 10/2009 | | WO | WO 0141919 A1 | 6/2001 |
| FR | 2935699 A1 | 3/2010 | | WO | WO 0186220 A2 | 11/2001 |
| FR | 2935968 A1 | 3/2010 | | WO | WO 02/26672 A2 | 4/2002 |
| GB | 14767 A | 0/1914 | | WO | WO 03/064357 | 8/2003 |
| GB | 406345 | 8/1932 | | WO | WO 2004/056758 | 7/2004 |
| GB | 404938 A | 1/1934 | | WO | WO 2005021476 A1 | 3/2005 |
| GB | 467481 A | 6/1937 | | WO | WO 2005054167 A1 | 6/2005 |
| GB | 541357 A | 11/1941 | | WO | WO 2005/097722 | 10/2005 |
| GB | 679536 A | 9/1952 | | WO | WO 2005/115954 | 12/2005 |
| GB | 702143 A | 1/1954 | | WO | WO 2005/116004 | 12/2005 |
| GB | 736641 A | 9/1955 | | WO | WO 2006020234 A1 | 2/2006 |
| GB | 799567 A | 8/1958 | | WO | WO 2006/100311 A2 | 9/2006 |
| GB | 984446 A | 2/1965 | | WO | WO 2006/100312 A2 | 9/2006 |
| GB | 984633 A | 3/1965 | | WO | WO 2006/100313 A2 | 9/2006 |
| GB | 1046521 A | 10/1966 | | WO | WO 2006/100314 A1 | 9/2006 |
| GB | 1083594 A | 9/1967 | | WO | WO 2006/100315 A2 | 9/2006 |
| GB | 1286893 A | 8/1972 | | WO | WO 2006/100316 A1 | 9/2006 |
| GB | 1387668 A | 3/1975 | | WO | WO 2006/100317 A1 | 9/2006 |
| GB | 1 493 538 | 4/1975 | | WO | WO 2006/100318 A2 | 9/2006 |
| GB | 1414976 A | 11/1975 | | WO | WO 2006/100319 A1 | 9/2006 |
| GB | 2173496 A | 10/1986 | | WO | WO 2006/100320 A2 | 9/2006 |

| | | | |
|---|---|---|---|
| WO | WO 2006/106153 A2 | 10/2006 |
| WO | WO 2006/106154 A1 | 10/2006 |
| WO | WO 2006/106155 A2 | 10/2006 |
| WO | WO 2007/054505 A2 | 5/2007 |
| WO | WO2007/144335 | 12/2007 |
| WO | WO 2008/101866 | 8/2008 |
| WO | WO2008/107468 | 9/2008 |
| WO | WO 2008/110588 | 9/2008 |
| WO | WO2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO2009/000773 | 12/2008 |
| WO | WO 2009/016149 A2 | 2/2009 |
| WO | WO 2009026212 A1 | 2/2009 |
| WO | WO 2009/043796 A1 | 4/2009 |
| WO | WO2009/043796 A1 | 4/2009 |
| WO | WO 2009/077528 | 6/2009 |
| WO | WO 2009/077528 A1 | 6/2009 |
| WO | WO 2009/095429 A1 | 8/2009 |
| WO | WO 2009/121853 | 10/2009 |
| WO | WO2009/121853 A1 | 10/2009 |
| WO | WO 2010/029039 | 3/2010 |
| WO | WO 2010/029039 A1 | 3/2010 |
| WO | WO 2010/029153 | 3/2010 |
| WO | WO 2010/029153 A1 | 3/2010 |
| WO | WO 2010/066660 | 6/2010 |

OTHER PUBLICATIONS

Perry's Chemical Engineers Handbook 7th Ed., 11th Section, 1997, pp. 11.1-11.118 (submitted into two parts).
Perry's Chemical Engineers Handbook 7th Ed., 13th Section, 1997, pp. 13.1-13.108.
Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Application No. FR 06.05325 filed Jun. 14, 2006 by Solvay S.A.—priority document to EP2007/55742 published as WO 2007/144335 (attached herein) 17 pgs.
Application No. FR 07.53863 filed Mar. 15, 2007 by Solvay S.A. and published as FR2913683, 19 pgs (attached herein)—priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorohydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono- and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevier Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. As Amended by Act No. 93/2004, Coll. To the extent of Annex No. 4 (SPOLEK) Nov. 30, 2004, 80 pgs.
Documentation Under Act. No. 100/2001 Coll. As Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.
The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.

Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
U.S. Appl. No. 11/915,046, filed Nov. 20, 2007, Krafft, et al.
U.S. Appl. No. 60/734,636, filed Nov. 8, 2005.
U.S. Appl. No. 11/915,088, filed Nov. 20, 2007, Krafft, et al.
U.S. Appl. No. 60/560,676, filed Apr. 8, 2004, Gilbeau, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.
U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 61/007,661, filed Dec. 14, 2007, Boulos, et al.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Kleiboehmer W., et al, Solvay Werk Rheinberg: Integrierte Prozesse Separierte Abwasserbehandlungen—Gewaesserschutz, Wasser, Abwasser 200 (Wissenschaftlich-technische Mitteilungen des Instituts Zur Foerderung der Wasserguerte- und Wasserm engenwirtschaft e; V;—2005 p. 81/-8/5., vol. 5.
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.ip/Ietc/Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.
Laine, D.F. et al. "The destruction of organic pollutants under mild reaction conditions; A review" Michochemical Journal, vol. 85, No. 2, 2007 pp. 183-193; available online Aug. 17, 2006; 12 pp.
Production and Prospect of the World Natural Glycercl by Zhu Shiyong, Cereals and Oils, vol. 1, 1997, pp. 33-38 (No English Translation).
Vinnolit; Vinnolit receives EU grant tor water recycling project: Press Release. 2008. http://www.vinnolit.de/vinnolit.nsf/id/EN_Vinnolit_receives_EU_grant_for_water_recycling_project_.
N.W. Ziets, Journal of American Oil Chemists' Society, Nov. 1956, vol. 33, pp. 556-565.
Perry's Chemical Engineers Handbook, Sixth Edition, McGraw Hill Inc., (1984) Section 18.

Vol. B3: Unit Operations II of Ullmann's Encyclopedia of Industrial Chemistry, Fifth Completely Revised Edition, Published by VCH, 1988.
W. Giger et al., "14C/12C-Ratios in Organic Matter and Hydrocarbons Extracted from Dated Lake Sediments," Nuclear Instruments and Methods in Physics Research B5 (1984), 394-397, XP-002631954.
Jurgen O. Metzger, "Fats and Oils as Renewable Feedstock for Chemistry," Eur. J. Lipid Sci. Technol. (2009), 111, 865-876. XP-002631953.
Bruce M. Bell, "Glycerin as a Renewable Feedstock for Epichlorohydrin Production. The GTE Process," Clean-Soil, Air, Water, vol. 36, No. 6, (2008) pp. 657-661. XP-002631952.
[Unknown Author], Kirk Othmer Encyclopedia of Chemical Technology—vol. 2, p. 156, John Wiley and Sons, 1992.
Horsley, Lee H.—"Azeotropic Data-III", The Dow Chemical Co., Midland, MI, American Chemical Society 1973; pp. 1-4; 4 pgs.
Suzawa, Yoshikazu, et al—"Incineration System for Waste Liquid Containing Chlorinated Organic Compounds", Chemical Apparatuses, 1981, vol. 23, No. 11; 34 pgs; Translation in English provided.
D'Alonzo, R.P., et al—"Glyceride Composition of Processed Fats and Oils As Determined by Glass Capillary Gas Chromatography", Journal of American Oil Chemists' Society, 1982, vol. 59, No. 7, pp. 292-295; 4 pgs.
Chemical Engineering Handbook, $6^{th}$ Revised Edition, 2001, pp. 1-36; 56 pgs; Translation in English provided.
"Electrolytic cell test for electrolysis of epoxy sewage salt to prepare chlor-alkali", Process Equipment Department of Research Institute of Chloro-Alkali, Shengyang Chemical Plant, Liaoning Chemical Industry, Issue n°2, pp. 32-37, published Dec. 31, 1981; 17 pgs; Translation in English provided.
Chengxin, Ren, et al—"Analysis on the Composition of the Byproduct During the Manufacturing Process of S-Epichlorohydrin by GC-MS", Chemical Analysis and Meterage, 2003, vol. 12, Issue No. 3, pp. 25-26; 6 pgs; Translation in English provided.
Encyclopedia of Chemical Technology, vol. 5, Nov. 1993; 6 pgs; Translation in English provided.
"Manufacture and use of epoxy resin", edited by Shanghai Resin Factory, published by China Petrochemical Press, First Edition, Oct. 1974; 16 pgs; Translation in English provided.
Gilman, Henry, et al—"Organic synthesis", Part 1, published by Scientific Publishing, 1957 (with abstract); 4 pgs.
Handbook of Chemical Products, Heavy Organic Chemicals, Second edition, published by Chemical Industry Press, Jan. 1995; 13 pgs; Translation in English provided.
Kiseleva, R. A., et al—"Study of the Interaction of Dibasic Acids with Glycerol", J. App. Chem. USSR, 1971, vol. 44, pp. 2086-2090; 5 pgs.
Handbook of Corrosion Data and Material Selection, published by Chemical Industry Press, edited by Jingyi Zuo, Yu Zuo; First edition, Oct. 1995, 5 pgs; Translation in English provided.
Handbook of Azeotropic Mixture, edited by Information Department of Comprehensive Scientific Technology Research Institution of Fushun City, 1993; 8 pgs; Translation in English provided.
"Industry Chemical Reaction and Application", published by Chinese Scientific Technology University Press, 1999; 4 pgs; Translation in English provided.
"Epoxy resin", published by Shanghai People's Publishing House, 1971; Translation in English provided; 21 pgs.
Boschan, Robert, et al—"The Role of Neighboring Groups in Replacement Reactions. XXI. Front-side Participation of Acetoxy Group. Catalytic Effect of Acetic Acid on the Reaction of Glycols with Hydrogen Chloride", Journal of the American Chemical Society, 1956, vol. 78, pp. 4921-4925; 5 pgs.
Encyclopedia for Chinese Adult Education, 1994, p. 623; 10 pgs; Translation in English provided.
[Unknown Author]—New Experimental Chemical Course 1, Basic Operation I, Section 4, Separation and Purification, pp. 251-252 (issued on Sep. 20, 1975) with English translation from Shiga International Patent Office, 3 pgs.
March, Jerry—"Reactions, Mechanisms & Structure", Advanced Organic Chemistry, $4^{th}$ Ed., 1992, pp. 889, 908 and 937; 5 pgs.
[Unknown Author]—Bulletin de la Société Chimique de Paris—"Analyse des Travaux de Chimie Pure et Appliquée", G. Masson, Editor, Paris, Jul. 4, 1873, Novelle Série, Tome XIX, pp. 97-99; 4 pgs ; comments regarding Friedel & Silva's work on middle of p. 98.

Neuberg, Irene Stephanie—"A New Way of Preparing Glyceraldehyde from Glycerol", Kaiser Wilhelm Institute in Berlin for Biochemi-Dahlem, 1930; 3 pgs; Includes abstract in English.

Krausz, Francois—'Recherches sur les Aldehydes Substitues en α en β. α and β Substituted Aldehydes', University Strasbourg, France ; Ann Chim 12, Nov.-Dec. 1949, 4, pp. 811-831, 23 pgs ; Includes abstract in English.

[Unknown Author]—"Glycerine—An Overview "—by The Soap and Detergent Association, Glycerine and Oleochemical Division, 1990; 27 pgs.

[Unknown Author]—"Commercial Synthesis of Glycerol Begins a New Shell Chemical Corp Plant—A staff Report"; Chemical & Engineering News, 1948, vol. 26, No. 38, pp. 2770-2771; 2 pgs.

Fairbourne, Arthur, et al—"The Partial Esterification of Polyhydric Alcohols . Part XII . The Funstion of Ethylene-oxide Rings", J. Chem. Soc. 1932, republished 1965, pp. 1965-1972; 8 pgs.

Clarke, H.T., et al—"Epichlorohydrin", Organic Syntheses, Coll. vol. 1, pp. 233 (1941) ; vol. 3, p. 47 (1923); 2 pgs.

Braun, Geza—"Epichlorohydrin and Epibromohydrin", Organic Syntheses, Coll. vol. 2, p. 256 (1943) ; vol. 16, p. 30 (1936); 2 pgs.

Conant, J.B., et al —"Glycerol a.y-Dichlorohydrin", Organic Syntheses, Coll. vol. 1, p. 292 (1941); vol. 2, p. 29 (1922); 3 pgs.

Chavanne, G.—"Memoires Presentes a La Societe Chimique", English translation—"Reports Submitted to Chemical Firm", Bull. Soc. Chim. Fr. 1943, 1, EP 06 121 086; 16 pgs.

Schroder, Angela, et al—"Glycerol as a by-product of biodiesel production in Diets for ruminants", 1999, The Regional Institute, Institute of Animal Nutrition, Physiology and Metabolism, University of Kiel, Germany, 6 pgs.

[Unknown Author]—"Chemical Properties and Derivatives of Glycerol ", 1965, Glycerine Producer's Association, $1^{st}$ Edition, 23 pgs.

Busby, G.W., et al——"The Purification of Glycerin by Ion-Exchange", The Journal of the American Oil Chemists' Society, 1952, 3 pgs.

Lamborn, Leebert Lloyd—"Modern Soaps, Candles and Glycerin", $3^{rd}$ Edition, 1918, D. Van Nostrand Company, London, 12 pgs.

Knothe, Gerhard—"Historical perspectives on vegetable oil-based diesel fuels", Industrial Oils, 2001, vol. 12, pp. 1103-1107; 5 pgs.

Schuchardt, Ulf, et al—"Transesterification of Vegetable Oils: A Review", 1998, Braz. Chem Soc., vol. 9, No. 1, pp. 199-210; 12 pgs.

Claude, Sylvain—"Research of new outlets of glycerol-recent developments in France"—1999, Fett/Lipid, No. 3, Wiley-VCH Verlag GmbH, Weinheim, pp. 101-104; 4 pgs.

Prakash, Chandra B.—"A Critical Review of Biodiesel as a Transportation Fuel in Canada", 1998, GCSI—Global Change Strategies International Inc.; 119 pgs.

Fukuda, Hideki, et al—"Review—Biodiesel Fuel Production by Transesterification of Oils", 2001, Journal of Bioscience and Bioengineering; vol. 92, No. 5, pp. 405-416; 12 pgs.

Yong, K.C., et al—"Refining of Crude Glycerine Recovered From Glycerol Residue by Simple Vacuum Distillation", Dec. 2001, Journal of Oil Palm Research, vol. 13, No. 2, pp. 39-44, 6 pgs.

Ma Zengxin et al, "recovery of Polyglycerol from residues of Synthetic Glycerol" Riyong Huaxue Gongye, 1997, 4, 21023 (English Abstract only).

Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.

RD 436093, Aug. 10, 2000.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

Medium and Long-term Opportunities and Risks of the Biotechnological Production of Bulk Chemicals from renewable Resources—The Potential of White Technology—The BREW project—Final Report—prepared under the European Commission GRXTH Programme (DG Research) Ulrecht, Sep. 2006 (pp. 29-31).

Ullmann's Encyclopedia Industrial Chemistry, $5^{th}$ Ed. vol. A6 (1988) pp. 401-477.

Polymer Science Dictionary, M.S.M., Elsevier Applied Chemistry, London & New York, 1989 p. 86.

Perry's Chemical Engineers' Handbook, $6^{th}$ Edition, Section 21, pp. 21-55.

M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.

Ying Ling Liu, "Epoxy Resins from Novel Monomers with a Bis-(9,10-dihydro-9-oxe-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

GLYCEROL-BASED PRODUCT, PROCESS FOR OBTAINING SAME AND USE THEREOF IN THE MANUFACTURING OF DICHLOROPROPANOL

CROSS-REFERENCE TO RELATED APPLICATIONS

The present patent application is a U.S. national stage application under 35 U.S.C. §371 of International Application No. PCT/EP2008/067624 filed Dec. 16, 2008, which claims the benefit of the French Patent application FR 07/59891 filed on Dec. 17, 2007, the content of which is incorporated herein by reference.

The present invention relates to a product based on glycerol (1,2,3-propanetriol), to a process for obtaining it and to the use of the product in the manufacture of dichloropropanol and of derived products such as epichlorohydrin and the products derived from epichlorohydrin.

Dichloropropanol, for example, is a reaction intermediate in the manufacture of epichlorohydrin and epoxy resins (Kirk-Othmer Encyclopedia of Chemical Technology, Fourth Edition, 1992, Vol. 2, page 156, John Wiley & Sons, Inc.).

According to known processes, dichloropropanol can be obtained in particular by hypochlorination of allyl chloride, by chlorination of allyl alcohol and by hydrochlorination of glycerol. The latter process exhibits the advantage that the dichloropropanol can be obtained starting from fossil raw materials or renewable raw materials and it is known that petrochemical natural resources, from which the fossil materials originate, for example oil, natural gas or coal, available on Earth are limited.

The known processes have the problem of resulting in the accumulation of nitrogen-based products in various steps of the process of manufacturing dichloropropanol, more particularly in the recycle streams, and in the purges of said streams. These nitrogen-containing compounds contribute to the formation of nitrogen oxides ($NO_x$) in certain treatments of said streams, such as high-temperature oxidations (HTOs). The formation of $NO_x$ necessitates equipping these operations with a unit for abatement of these $NO_x$. This is because $NO_x$ contribute to the formation of photochemical smog (a significant form of atmospheric pollution) and to the formation of acid rain.

The invention aims to solve this problem by providing a novel glycerol-containing product that does not lead to the aforementioned problem when it is used in a process for manufacturing dichloropropanol.

The invention therefore relates to a product that contains glycerol and at least one nitrogen-containing compound and of which the total content of nitrogen-containing compound expressed as elemental nitrogen (N) is less than or equal to 1 g N/kg of product.

Molecular nitrogen $N_2$ is not a nitrogen-containing compound according to the invention.

One of the main features of the invention lies in the low content of nitrogen-containing compounds of the glycerol-containing product. The advantage of using, for the manufacture of dichloropropanol, a product that contains glycerol and a low content of nitrogen-containing product according to the invention is in avoiding the accumulation of nitrogen-containing products in the various steps of the process, more particularly in the recycle streams, and in the purges of said streams. The low content of nitrogen-containing compounds of the purges allows them to be treated in high-temperature oxidation (HTO) processes with a reduced production of nitrogen oxides. This makes it possible to reduce the size of an abatement unit for these nitrogen oxides at the outlet of the HTO process, or even to completely eliminate such a unit.

In the product according to the invention, the glycerol content is generally greater than or equal to 500 g of glycerol per kg of product, preferably greater than or equal to 750 g/kg, more preferably greater than or equal to 900 g/kg, even more preferably greater than or equal to 950 g/kg and most particularly preferably greater than or equal to 990 g/kg.

In the product according to the invention, the nitrogen-containing compound may be an inorganic compound or an organic compound. The expression "inorganic compound" is understood to mean the compounds for which the molecule does not contain a carbon-carbon bond or a carbon-hydrogen bond. The expression "organic compound" is understood to mean the compounds for which the molecule contains at least one carbon-carbon bond or one carbon-hydrogen bond.

The inorganic nitrogen-containing compound may be chosen from ammonia, hydrazine, chloramines, inorganic ammonium salts, metallic or ammonium nitrates, nitrites, cyanates, isocyanates or isothiocyanates, and mixtures thereof.

The organic nitrogen-containing compound may be chosen from the nitrogen-containing compounds present in cells of plant origin, preferably from amines, urea, proteins, peptides, amino acids, nucleic acids, glucosinolates and degradation products thereof (isothiocyanates, thiocyanates, nitriles, oxazolidinethiones), nitrogen-containing phospholipids, chlorophyll, sinapine, and mixtures thereof.

Examples of nitrogen-containing phospholipids are phosphatidylcholine, phosphatidylserine and phosphatidylethanolamine.

Examples of free amino acids or amino acids that can be incorporated in the composition of peptides or of proteins are alanine, arginine, aspartic acid, cystine, glutamic acid, glycine, histidine, isoleucine, leucine, lysine, methionine, phenylalanine, proline, serine, threonine, tryptophan, tyrosine and valine.

Examples of glucosinolates are sinigrin, gluconapin, glucobrassicanapin, glucorucin, glucoberteroin, glucoraphanin, glucoalyssin, gluconasturtiin, progoitrin, napoleiferin, glucobrassicin and neoglucobrassicin.

The nitrogen-containing compound may originate from the glycerol manufacturing process, for example from plant oils used to manufacture glycerol or else from steam corrosion inhibitors, certain heating operations possibly taking place by injection of live steam into the oils or the glycerol for example. These corrosion inhibitors are generally hydrazine or amines, such as isopropylamine, for example.

In the product according to the invention, the total content of nitrogen-containing compound expressed as elemental nitrogen is preferably less than or equal to 0.5 g N/kg, more preferably less than or equal to 0.1 g N/kg, even more preferably less than or equal to 0.05 g N/kg, more preferably still less than or equal to 0.03 g N/kg, and most particularly preferably less than or equal to 0.01 g N/kg. This content is generally greater than or equal to 0.1 mg N/kg.

The glycerol-based product according to the invention generally contains diols, usually at least one diol, as described in Application FR 07/56125 in the name of Solvay SA, from page 1, line 18 to page 2, line 7, and the content of which is incorporated here by reference.

The diol is preferably chosen from 1,2-ethanediol (ethylene glycol), 1,2-propanediol (propylene glycol), 1,3-propanediol, 1,2-butanediol, 2,3-butanediol, 1,4-butanediol or a mixture of at least two of them. 1,3-propanediol is particularly preferred.

In the glycerol-based product according to the invention, the diol content is generally greater than or equal to 0.001 g diol/kg of product and less than or equal to 100 g diol/kg of product. This content is often less than or equal to 90 g/kg, commonly less than or equal to 50 g/kg, frequently less than or equal to 10 g/kg, usually less than or equal to 1 g/kg, commonly less than or equal to 0.5 g/kg and frequently less than or equal to 0.2 g/kg. This amount is often greater than or equal to 0.005 g/kg, frequently greater than or equal to 0.01 g/kg, commonly greater than or equal to 0.04 g/kg and usually greater than or equal to 0.1 g/kg.

The glycerol-based product according to the invention generally contains glycerol alkyl ethers, usually at least one glycerol alkyl ether, as described in Application WO2007/144335 in the name of Solvay SA, from page 2, line 6 to page 3, line 25, and the content of which is incorporated here by reference. Glycerol methyl ethers are preferred.

The content of glycerol alkyl ethers is generally less than or equal to 90 g/kg, often less than or equal to 50 g/kg, frequently less than or equal to 10 g/kg, commonly less than or equal to 5 g/kg, usually less than or equal to 1 g/kg, more commonly less than or equal to 0.5 g/kg and more frequently less than or equal to 0.2 g/kg. This content is generally greater than or equal to 0.005 g/kg, frequently greater than or equal to 0.01 g/kg, often greater than or equal to 0.04 g/kg and more frequently greater than or equal to 0.1 g/kg.

The glycerol-based product according to the invention may also comprise monoalcohols, usually at least one monoalcohol, such as the monoalcohols described in Application WO2007/144335 in the name of Solvay SA, from page 3, lines 26 to 31, and the content of which is incorporated here by reference.

These monoalcohols are generally present in a content greater than or equal to 0.001 g/kg of product, and often greater than or equal to 0.01 g/kg. This content is generally less than 20 g/kg of product and often less than or equal to 2 g/kg of product.

The glycerol-based product according to the invention may also comprise water in a content generally greater than or equal to 0.1 g/kg and less than or equal to 100 g/kg. This amount is often less than or equal to 50 g/kg and more preferably less than or equal to 20 g/kg.

The glycerol-based product according to the invention may also comprise alkyl esters of fatty acids, usually at least one alkyl ester of fatty acids, glycerol esters, generally at least one glycerol ester, and salts, commonly at least one salt, as described in Application WO2007/144335 in the name of Solvay SA, from page 5, lines 12 to 20.

These esters are generally present in a content greater than or equal to 0.1 g/kg of product, often greater than or equal to 1 g/kg and frequently greater than or equal to 5 g/kg. This content is generally less than 50 g/kg of product, and often less than or equal to 30 g/kg of product, and more often less than or equal to 10 g/kg of product.

These salts are generally present in a content greater than or equal to 0.0005 g/kg of product, often greater than or equal to 0.001 g/kg and frequently greater than or equal to 0.01 g/kg. This content is generally less than 10 g/kg of product, and often less than or equal to 1 g/kg of product, and more often less than or equal to 0.1 g/kg of product.

The diols, glycerol alkyl ethers, monoalcohols, water, alkyl esters of fatty acids, glycerol esters and salts may be by-products of glycerol manufacturing processes such as, for example, the processes for conversion of oils or fats of plant or animal origin via transesterification, saponification or hydrolysis reactions.

The glycerol-based product according to the invention may be obtained starting from fossil raw materials or starting from renewable raw materials, preferably starting from renewable raw materials, as described in WO 2005/054167 of SOLVAY SA, the content of which is incorporated herein by reference, and especially the passages from page 1, line 26, to page 4, line 2.

The glycerol-based product according to the invention may also be obtained starting from fossil raw materials or starting from renewable raw materials, preferably starting from renewable raw materials, as described in WO 2006/100312 of SOLVAY SA, the content of which is incorporated herein by reference, and especially the passages from page 3, line 29, to page 5, line 24.

The glycerol-based product according to the invention may also be obtained starting from fossil raw materials or starting from renewable raw materials, preferably starting from renewable raw materials, as described in PCT/EP2008/057876 of SOLVAY SA, the content of which is incorporated herein by reference, and especially the passages at page 10, lines 16 to 23, and at page 11, lines 4 to 25.

The glycerol-based product according to the invention may have an alkali metal and/or alkaline earth metal content as described in WO 2006/100315 of SOLVAY SA, the content of which is incorporated herein by reference, and especially the passages from page 7, line 11, to page 9, line 10.

The glycerol-based product according to the invention may contain elements other than alkali metals and alkaline earth metals as described in WO 2006/100319 of SOLVAY SA, the content of which is incorporated herein by reference, especially the passages from page 2, line 3 to 8, and from page 6, line 20, to page 9, line 14.

The glycerol-based product according to the invention contains generally an amount of heavy compounds other glycerol and whose boiling temperature under a pressure of 1 bar absolute is at least 15° C. greater than the boiling temperature of dichloropropanol as described in WO 2006/1000316 of SOLVAY SA the content of which is incorporated herein by reference, especially the passages from page 15, line 32, to page 17, line 33.

The glycerol-based product according to the invention may contain glycerol oligomers as described in FR 08/52206 of SOLVAY SA the content of which is incorporated herein by reference, especially the passages from page 1, line 19, to page 4, line 18.

The invention also relates to a process for preparing the glycerol-containing product and at least one nitrogen-containing compound and of which the total content of nitrogen-containing compound expressed as elemental nitrogen is less than or equal to 1 g N/kg, comprising the following steps:

a) the seeds of a plant are subjected to a pressing operation so as to obtain an oil of plant origin;
b) the plant oil is subjected to a transesterification operation in the presence of methanol so as to obtain glycerol containing at least one nitrogen-containing compound and of which the total content of nitrogen-containing compound expressed as elemental nitrogen is greater than 1 g N/kg; and
c) the glycerol-containing product from step b) is subjected to a supplementary step c) in which a fraction of the glycerol obtained in step b) is subjected to at least one purification treatment so as to obtain a product that contains glycerol and at least one nitrogen-containing compound and of which the total content of nitrogen-containing compound expressed as elemental nitrogen is less than or equal to 1 g N/kg of product.

The treatment from step c) may be carried out under reduced pressure. The treatment may be chosen from the group consisting of evaporative concentration, evaporative crystallization, distillation, fractional distillation, stripping, liquid/liquid extraction operations, and any combination of at least two of them.

The term "evaporative concentration" is understood to mean a process of partial evaporation of the product that makes it possible to concentrate the residual product to less volatile entities. The term "evaporative crystallization" is understood to mean a process resulting in the crystallization of a compound by removing, by vaporization, a compound that promotes its dissolution in the medium. These processes are described in "Perry's Chemical Engineers' Handbook" in the $11^{th}$ section of the $7^{th}$ edition.

The term "distillation" is understood to mean the type of separation conventional in chemical engineering and described, for example, in "Perry's Chemical Engineers' Handbook" in the $13^{th}$ section of the $7^{th}$ edition.

The term "fractional distillation" is understood to mean a series of distillations where the distillate is withdrawn batchwise.

The term "stripping" is understood to mean the separation of a substance by entrainment using the vapour of a pure material. In the process according to the invention, this material can be any compound which is inert with respect to glycerol, such as, for example, steam, air, nitrogen and carbon dioxide.

The term "liquid/liquid extraction" is understood to mean bringing into contact with an appropriate completely or partially immiscible solvent that makes it possible to selectively extract the desired compounds, optionally according to a countercurrent process, as described in "Perry's Chemical Engineers' Handbook" in the $15^{th}$ section of the $7^{th}$ edition.

The stripping, evaporative concentration, evaporative crystallization, liquid/liquid extraction and distillation treatments may be combined, for example in a stripping column surmounted by a distillation section or in a partial evaporator supplying a distillation column or by combining a liquid/liquid extraction, stripping of the residual solvent contained in the glycerol-enriched stream and distillation of the solvent enriched with extracted compounds.

The diols, monoalcohols and the glycerol alkyl ethers are recovered in the distilled, evaporated or stripped fraction and the purified glycerol-based product constitutes an intermediate cut from the distillation, evaporation or stripping treatment. The major part of the nitrogen-containing impurities constitutes the residue from the treatment.

When the treatment consists of a partial evaporation of the product, the temperature of the glycerol-rich zone is generally greater than or equal to 0° C., often greater than or equal to 80° C. and frequently greater than or equal to 100° C. This temperature is generally less than or equal to 280° C., often less than or equal to 250° C., and frequently less than or equal to 200° C. The temperature in the glycerol-depleted zones is generally greater than or equal to −20° C., preferably greater than or equal to −10° C., particularly preferably greater than or equal to 0° C. This temperature is generally at most equal to the temperature of the glycerol-rich zone, preferably at least 5° C. below this temperature, particularly preferably at least 10° C. below this temperature.

When the treatment is carried out by liquid/liquid extraction, the temperature is generally greater than or equal to 20° C., preferably greater than or equal to 40° C., more particularly greater than or equal to 50° C. This temperature is generally less than or equal to 200° C., preferably less than or equal to 150° C. and more particularly preferably less than or equal to 120° C.

The treatment pressure is generally greater than or equal to 0.001 mbar. This pressure is generally less than or equal to 1 bar, often less than or equal to 0.5 bar, frequently less than or equal to 0.3 bar and more specifically less than or equal to 0.25 bar. When the treatment comprises a separate evaporation step, the latter is generally carried out at a pressure less than or equal to 2 bar absolute, preferably at a pressure less than or equal to 1 bar absolute, particularly preferably at a pressure less than or equal to 0.5 bar absolute. It is generally carried out at a pressure greater than or equal to 0.1 mbar, preferably at a pressure greater than or equal to 0.2 mbar. When the evaporation step is combined with a distillation or fractional distillation step, it is carried out at a pressure at least equal to the pressure of the step carried out at the lowest pressure, preferably at a pressure at least 10 mbar greater than the pressure of the step carried out at the lowest pressure. The stripping step is generally carried out at a pressure less than or equal to 5 bar, preferably less than or equal to 2 bar.

In the distillation treatments with or without stripping, the reflux ratio is generally greater than or equal to 1%, often greater than or equal to 5% and frequently greater than or equal to 10%. This reflux ratio is generally less than or equal to 99% and often less than or equal to 50%. The expression "reflux ratio" is understood to mean, for a continuous distillation, the ratio between the flow rate of the vaporized fraction to the reboiler and the flow rate of the residue.

The expression "reflux ratio" is understood to mean, for a batchwise, fractional distillation, the ratio of the amount vaporized relative to the final residue.

The amount of the fraction distilled is generally less than or equal to 300 g/kg, often less than or equal to 100 g/kg of the glycerol-based product.

The distillation, fractional distillation or stripping treatment may be preceded or followed by an operation which may, for example, be a settling, centrifugation, filtration, adsorption or ion-exchange operation. When it is a settling operation, the operation can be improved by passing through a coalescer. The adsorption operation is preferably an operation for adsorption on activated carbon.

The invention also relates to a process for manufacturing dichloropropanol in which a product that contains glycerol and at least one nitrogen-containing compound, of which the total content of nitrogen-containing compound expressed as elemental nitrogen is less than or equal to 1 g N/kg, is reacted with a chlorinating agent.

The chlorinating agent generally comprises hydrogen chloride. The hydrogen chloride can be gaseous hydrogen chloride, an aqueous hydrogen chloride solution or a mixture of the two.

The chlorinating agent is as described in Patent Application WO2005/054167, from page 4, line 32, to page 5, line 18, in the name of Solvay SA, the content of which is incorporated here by reference.

In the process for manufacturing dichloropropanol according to the invention, the hydrogen chloride is often a gas or a mixture of a gas and an aqueous solution of hydrogen chloride. The hydrogen chloride may at least partially be obtained from processes such as described in WO 2005/054167 of SOLVAY SA, the content of which is incorporated herein by reference, especially the passages from page 4, line 32, to page 5, line 35.

The hydrogen chloride may at least partially be obtained from processes such as described in WO 2006/106153 of SOLVAY SA, the content of which is incorporated herein by reference, especially the passages from page 2, line 10, to page 3, line 20, and from page 11, line 1 to page 18, line 29.

The hydrogen chloride may at least partially be obtained from processes such as described in WO 2007/144335 of SOLVAY SA, the content of which is incorporated herein by reference, especially the passages from page 12, line 14, to page 14, line 21.

In the process for manufacturing dichloropropanol according to the invention, the hydrogen chloride may purified such as described in FR 08/56138 of SOLVAY SA, the content of which is incorporated herein by reference, especially the passages from page 2, line 33, to page 16, line 21.

In the process for manufacturing dichloropropanol according to the invention, the reaction between glycerol and the chlorinating agent the hydrogen chloride may be carried out in a reaction medium such described in WO 2006/106154 of SOLVAY SA, the content of which is incorporated herein by reference, especially the passages from page 14, line 15, to page 17, line 10.

The reaction with the chlorinating agent may be carried out in the presence of a catalyst, preferably a carboxylic acid or a carboxylic acid derivative, as described in Patent Application WO 2005/054167, from page 6, line 24, to page 7, line 35 in the name of Solvay SA, the content of which is incorporated here by reference. Succinic, glutaric, adipic, suberic, sebacic, dodecanoic, citric and butanetetracarboxylic acids and derivatives thereof such as acid chlorides, anhydrides, esters and salts, are examples of catalysts. Carboxylic acid derivatives that contain nitrogen such as, for example, amides and nitriles, are not considered to be carboxylic acid derivatives that can be used as catalysts.

The reaction with the chlorinating agent may be carried out for a catalyst concentration, at a temperature, at a pressure and at a residence time such described in WO 2005/054167 of SOLVAY SA, the content of which is incorporated herein by reference, especially the passages from page 8, line 1, to page 10, line 10.

The reaction with the chlorinating agent may be carried out such described in WO 2007/054505 of SOLVAY SA, the content of which is incorporated herein by reference, especially the passages from page 1, line 24 to page 6, line 18.

The process for manufacturing dichloropropanol according to the invention may be carried in equipments made of or coated with materials which are resistant to the corrosion by the chlorinating agent under the process conditions, such as described in WO 2005/054167 of SOLVAY SA, the content of which is incorporated herein by reference, especially the passages from page 6, line 3 to 23.

The process for manufacturing dichloropropanol according to the invention may be carried in equipments made of or coated with materials which are resistant to the corrosion by the chlorinating agent under the process conditions, such as described in WO 2006/100317 of SOLVAY SA, the content of which is incorporated herein by reference, especially the passages from page 23, line 22, to page 27, line 25.

The process for manufacturing dichloropropanol according to the invention may be carried in equipments made of or coated with materials which are resistant to the corrosion by the chlorinating agent under the process conditions, such as described in PCT/EP2008/062845 of SOLVAY SA, the content of which is incorporated herein by reference, especially the passages from page 1, line 30, to page 9, line 17, and from page 19, line 25, to page 20, line-33.

The chlorination reaction is preferably carried out in a liquid reaction medium.

The chlorination reaction may be carried out in the presence of a solventsuch described in WO 2005/054167 of SOLVAY SA, the content of which is incorporated herein by reference, especially the passages at page 11, line 12 to 36.

However, the solvent can not comprise nitrogen in its molecule.

The reaction with the chlorinating agent may be carried out in the presence of a liquid phase comprising heavy compounds other than glycerol such described in WO 2006/100316 of SOLVAY SA, the content of which is incorporated herein by reference, especially the passages at page 2, lines 18 to 25 and from page 15, line 32, to page 17, line 33. Heavy-compounds that contain nitrogen are not considered as heavy compounds that can be present in the liquid phase.

The reaction with the chlorinating agent may be carried out under stiffing with a stiffing system such described in PCT/EP2008/056688 of SOLVAY SA, the content of which is incorporated herein by reference, especially the passages from page 1, line 30, to page 2, line 33, and from page 6, line 22, to page 14, line 31.

The reaction with the chlorinating agent may be carried out in a liquid reaction medium such described in WO 2006/106154 of SOLVAY SA, the content of which is incorporated herein by reference, especially the passages from page 1, line 29, to page 2, line 6, and from page 14, line 15, to page 17, line 10.

The reaction with the chlorinating agent may be carried out in a reactor the feeding of which is described in WO 2008/107468 of SOLVAY SA, the content of which is incorporated herein by reference, especially the passages from page 1, line 29, to page 4, line 27, and from page 5, line 34, to page 9, line 17.

The dichloropropanol formed can be separated from the other constituents of the reaction medium by any separation treatment, for example by distillation, stripping, extraction or adsorption. After this treatment, the other constituents of the reaction medium may be subjected to supplementary separation treatments and/or be recycled. Among the other constituents of the reaction medium are heavy products such as, for example, various chlorinated and/or esterified isomers of glycerol oligomers.

In the process for manufacturing dichloropropanol according to the invention, a separation of the dichloropropanol from the other compounds of the reaction mixture may be carried out such described in WO 2005/054167 of SOLVAY SA, the content of which is incorporated herein by reference, especially the passages from page 12, line 1, to page 17, line 20.

In the process for manufacturing dichloropropanol according to the invention, a separation of the dichloropropanol from the other compounds of the reaction mixture may be carried out such described in WO 2006/100312 of SOLVAY SA, the content of which is incorporated herein by reference, especially the passages at page 2, lines 3 to 10, at page 20, line 28 to page 28, line 20.

In the process for manufacturing dichloropropanol according to the invention, a separation of the dichloropropanol from the other compounds of the reaction mixture may be carried out according to methods such described in WO 2006/100313 of SOLVAY SA, the content of which is incorporated herein by reference, especially the passages at page 2, lines 1 to 23, and from page 21, line 7, to page 25, line 25.

In the process for manufacturing dichloropropanol according to the invention, a separation of the dichloropropanol from the other compounds of the reaction mixture may be carried out according to methods such described in WO 2006/100314 of SOLVAY SA, the content of which is incorporated herein by reference, especially the passages at page 2, lines 6 to page 3, line 4, and from page 18, line 33, to page 22, line 29.

In the process for manufacturing dichloropropanol according to the invention, a separation of the dichloropropanol from the other compounds of the reaction mixture may be carried out according to methods such described in WO 2006/100320 of SOLVAY SA, the content of which is incorporated herein by reference, especially the passages from page 1, line 30, to page 2, line 23 and from page 6, line 25, to page 10, line 28.

In the process for manufacturing dichloropropanol according to the invention, a separation of the dichloropropanol from the other compounds of the reaction mixture may be carried out according to methods such described in WO 2006/100315 of SOLVAY SA, the content of which is incorporated herein by reference, especially the passages at page 2, lines 3 to 29, and from page 23, line 3, to page 24, line 13.

In the process for manufacturing dichloropropanol according to the invention, a separation of the dichloropropanol from the other compounds of the reaction mixture may be carried out according to methods such described in WO 2008/110588 of SOLVAY SA, the content of which is incorporated herein by reference, especially the passages from page 1, line 31, to page 27, line 25.

In the process for manufacturing dichloropropanol according to the invention, the dichloropropanol is generally obtained as a mixture of 1,3-dichloropropan-2-ol and 2,3-dichloropropan-1-ol isomers such described in WO 2006/100319 of SOLVAY SA, the content of which is incorporated herein by reference, especially the passages from page 23, line 34, to page 24, line 29.

In the process for manufacturing dichloropropanol according to the invention may contain halogenated ketones such described in WO 2006/100311 of SOLVAY SA, the content of which is incorporated herein by reference, especially the passages at page 2, lines 22 to 34, and from page 22, line 8, to page 23, line 35.

In the process for manufacturing dichloropropanol according to the invention, water which have been in contact with equipment walls may be treated such described in FR 08/56059 of SOLVAY SA, the content of which is incorporated herein by reference, especially the passages from page 1, line 7, to page 16, line 34.

The advantage of using, for the manufacture of dichloropropanol, a product that contains glycerol and a low content of nitrogen-containing product according to the invention is in avoiding the accumulation of nitrogen-containing products in the various steps of the process, more particularly in the recycle streams, and in the purges of said streams. The low content of nitrogen-containing compounds of the purges allows them to be treated in high-temperature oxidation (HTO) processes with a reduced production of nitrogen oxides. This makes it possible to reduce the size of an abatement unit for these nitrogen oxides at the outlet of the HTO process, or even to completely eliminate such a unit.

The nitrogen oxides, in particular NO and $NO_2$, may combine with the volatile organic compounds (VOCs) in the presence of sunlight to form a photochemical smog, a significant form of atmospheric pollution, particularly in summer. These nitrogen oxides may also dissolve in atmospheric moisture to form nitric acid, a component of acid rain.

The invention also relates to a process in which the dichloropropanol obtained according to the process for manufacturing dichloropropanol according to the invention is subjected to a dehydrochlorination reaction in order to obtain epichlorohydrin.

In this process, another part of the dichloropropanol may be obtained by a process other than glycerol chlorination. This process may be chosen from allyl chloride hypochlorination and allyl alcohol chlorination processes.

The process for dehydrochlorinating the dichloropropanol may be such as described in WO 2005/054167 in the name of SOLVAY SA, the content of which is hereby incorporated by reference, more specifically the passage from page 19, line 12 to page 22, line 30.

The process for dehydrochlorinating the dichloropropanol may be such as described in WO 2006/100311 in the name of SOLVAY SA, the content of which is hereby incorporated by reference, more specifically the passages at page 2, lines 22 to 25, and from page 22, line 28 to page 23, line 35.

The process for dehydrochlorinating the dichloropropanol may be such as described in WO 2008/101866 in the name of SOLVAY SA, the content of which is hereby incorporated by reference, more specifically the passage from page 2, line 1 to page 13, line 16.

The process for dehydrochlorinating the dichloropropanol may be such as described in PCT/EP2008/057247 in the name of SOLVAY SA, the content of which is hereby incorporated by reference, more specifically the passages from page 9, line 22 to page 13, line 31.

The process for dehydrochlorinating the dichloropropanol may be such as described in PCT/EP2008/057245 in the name of SOLVAY SA, the content of which is hereby incorporated by reference, more specifically the passages from page 6, line 16, to page 7, line 22.

The process for manufacturing the epichlorohydrin may be integrated in a global scheme for preparing dichloropropanol such as described in WO 2006/106155 in the name of SOLVAY SA, the content of which is hereby incorporated by reference, more specifically the passages at page 2, lines 26 to 31, and from page 22, line 10 to page 23, line 19.

The process for dehydrochlorinating the dichloropropanol may also be carried out such as described in WO 2006/100318 in the name of SOLVAY SA, the content of which is hereby incorporated by reference, more specifically the passages at page 2, lines 23 to page 3, line 26, and from page 24, line 17 to page 31, line 18.

The process for dehydrochlorinating the dichloropropanol may also comprise a step of treating water effluents such as described in EP 08150925.9 in the name of SOLVAY SA, the content of which is hereby incorporated by reference, more specifically the passages from page 1, line 18 to page 12, line 10.

The invention also relates to the use of a product that contains glycerol and at least one nitrogen-containing compound, of which the total content of nitrogen-containing compound expressed as elemental nitrogen is less than or equal to 1 g N/kg, is reacted with a chlorinating agent, in a process for manufacturing dichloropropanol. The characteristics of the process for manufacturing dichloropropanol are such as described hereabove.

The invention finally relates to a manufacturing process in which the epichlorohydrin obtained in the process for manufacturing epichlorohydrin according to the invention, is subjected to a reaction with:
  at least one compound containing at least one active hydrogen atom, so as to obtain an epoxy derivative, selected from the group consisting of an epoxy resin, a glycidyl ether, a glycidyl ester, a glycidyl amide, a glycidyl imide, or any mixture of at leas two of them; or
  ammonia, an amine, a polyaminoamide or a polyimine, so as to obtain a coagulant; or
  a polyamine, a polyamide or a polyaminoamide, so as to obtain a water-resistant resin for the treatment of paper; or an amine or an amine salt, so as to obtain a cationizing agent; or a compound chosen from phosphoric acid, a phosphoric acid salt, a phosphorus oxychloride, a phosphoric acid ester, a phosphonic acid, a phosphonic acid ester, a phosphonic acid salt, a phosphinic acid, a phosphinic acid ester, a phosphinic acid salt, a phosphine oxide or a phosphine, so as to obtain a flame retardant; or a monoalcohol containing from 12 to 16 carbon atoms or an amine chosen from linear alkylamines, branched alkylamines, cycloalkylamines, alkoxyamines, amino alcohols, cyclic amines containing at least one nitrogen atom in a cyclic structure, an alkylenediamine, a polyetherdiamine or a polyalkylenepolyamine, so as to obtain auxiliaries that are incorporated into the composition of detergents; or an alkylene oxide, a phenylene oxide or to a reaction with an alkylene oxide, a phenylene oxide and a glycidyl ether or to a homopolymerization reaction, so as to obtain an epichlorohydrin elastomer.

The epichlorohydrin and the uses of epichlorhydrin may be such as described in PCT/EP2008/057247 in the name of SOLVAY SA, the content of which is hereby incorporated by reference, more specifically the passages from page 1, line 18 to page 9, line 21, and from page 31, line 31 to page 63, line 4.

The epichlorohydrin and the uses of epichlorhydrin may be such as described in PCT/EP2008/057246 in the name of SOLVAY SA, the content of which is hereby incorporated by reference, more specifically the passages from page 1, line 24 to page 10, line 14, and from page 13, line 3 to page 44, line 8.

EXAMPLE 1

According to the Invention

Figure 1:
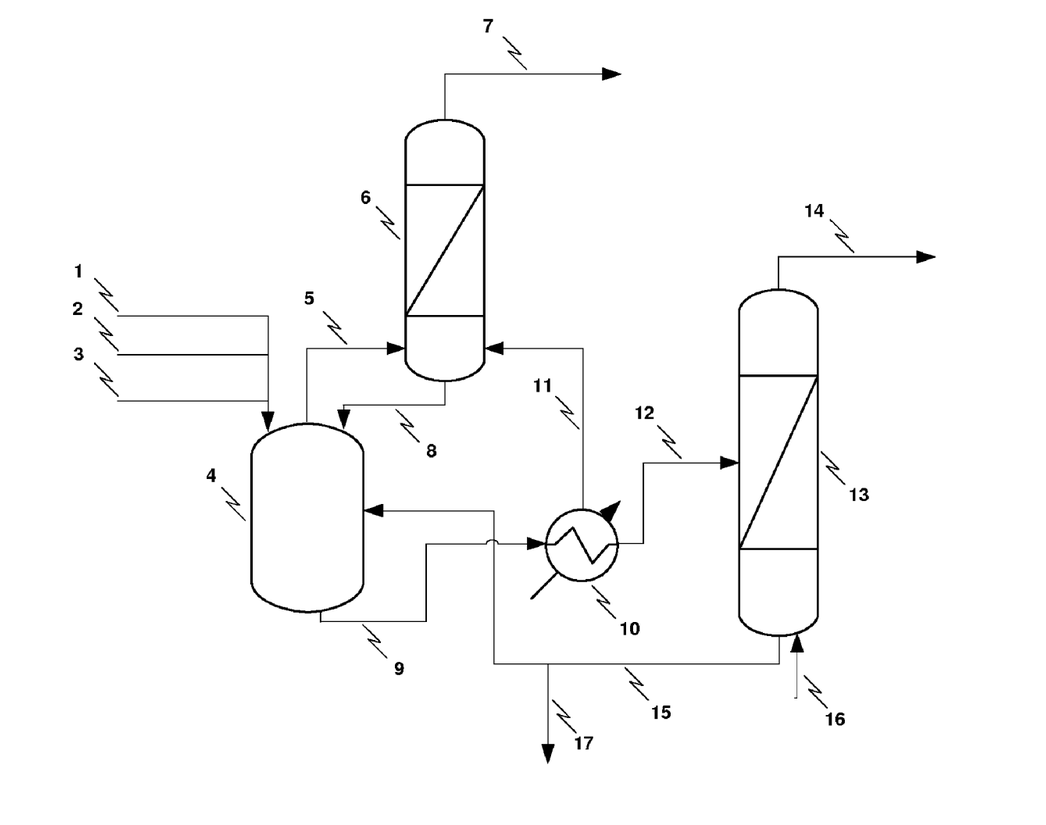

FIG. 1 represents one particular diagram of an installation which has been used to apply the dichloropropanol production process according to the invention.

A reactor (4) was continuously supplied, at 117° C. and at 1.14 bar absolute pressure, with glycerol containing 0.02 g N/kg via the line (1), a stream of hydrogen chloride via the line (2) and a stream of catalyst via the line (3). A distillation column (6) was supplied via the line (5) with a gas phase produced by the reactor (4); the residue from the column (6) was recycled via the line (8) to the reactor (4). The production stream (7) contains most of the water produced by the process and a first part of the dichloropropanol production. A liquid purge was drawn off from the reactor (4) via the line (9) and supplied an evaporator (10) where an operation of partial evaporation of the mixture was carried out by heating; the gas phase which contains most of the hydrogen chloride and most of the water from the stream (9) was recycled via the line (11) to the bottom of the column (6). A stripping column (13) was supplied by the liquid phase coming from the evaporator (10) via the line (12) and by a stream of nitrogen introduced via the line (16); a second part of the dichloropropanol production was collected at the top of the column (13) via the line (14) and the residue from the column (13) was recycled to the reactor (4) via the line (15). A purge of the mixture flowing in the line (15) was carried out batchwise via the line (17). The nitrogen content of the purge was 0.12 g N/kg.

The invention claimed is:

1. A product that contains glycerol and at least one nitrogen-containing compound and of which the total content of nitrogen-containing compound expressed as elemental nitrogen (N) is less than or equal to 1 g of nitrogen (N)/kg of product.

2. The product according to claim 1, wherein the total content of nitrogen-containing compound expressed as elemental nitrogen (N) is less than or equal to 0.03 g of nitrogen (N)/kg of product.

3. The product according to claim 1, comprising glycerol in a content greater than or equal to 500 g/kg of product.

4. The product according to claim 1, wherein the nitrogen-containing compound is chosen from the nitrogen-containing compounds present in cells of plant origin.

5. The product according to claim 4, wherein the nitrogen-containing compound is an organic compound selected from the group consisting of amines, urea, proteins, peptides, amino acids, nucleic acids, glucosinolates and degradation products thereof, nitrogen-containing phospholipids, chlorophyll, sinapine, and mixtures thereof.

6. A process for preparing the glycerol-based product according to claim 1, comprising the following steps:
   a) subjecting the seeds of a plant to a pressing operation so as to obtain an oil of plant origin;
   b) subjecting the plant oil to a transesterification operation in the presence of methanol so as to obtain a product that contains glycerol and at least one nitrogen-containing compound and of which the total content of nitrogen-containing compound expressed as elemental nitrogen (N) is greater than 1 g N/kg; and
   c) subjecting the glycerol-containing product from step b) to a supplementary step in which a fraction of the glycerol obtained in step b) is subjected to at least one purification treatment so as to obtain a product that contains glycerol and at least one nitrogen-containing compound and of which the total content of nitrogen-containing compound expressed as elemental nitrogen (N) is less than or equal to 1 g of nitrogen (N)/kg of product.

7. The process according to claim 6, wherein the purification treatment is optionally carried out under reduced pressure, and is selected from the group consisting of evaporative concentration, evaporative crystallization, distillation, fractional distillation, stripping, liquid/liquid extraction operations, and any combination of at least two of them.

8. The process for manufacturing dichloropropanol, wherein a glycerol-containing product according to claim 1 is reacted with a chlorinating agent.

9. The process according to claim 8, wherein the dichloropropanol is subjected to a dehydrochlorination reaction in order to obtain epichlorohydrin.

10. The process according to claim 8, wherein the epichlorohydrin obtained is subjected to a reaction with:
    at least one compound containing at least one active hydrogen atom, so as to obtain an epoxy derivative, selected from the group consisting of an epoxy resin, a glycidyl ether, a glycidyl ester, a glycidyl amide, a glycidyl imide or a mixture of at least two of them; or
    ammonia, an amine, a polyaminoamide or a polyimine, so as to obtain a coagulant; or
    a polyamine, a polyamide or a polyaminoamide, so as to obtain a water-resistant resin for the treatment of paper; or
    an amine or an amine salt, so as to obtain a cationizing agent; or
    a compound selected from the group consisting of phosphoric acid, a phosphoric acid salt, a phosphorus oxychloride, a phosphoric acid ester, a phosphonic acid, a phosphonic acid ester, a phosphonic acid salt, a phosphinic acid, a phosphinic acid ester, a phosphinic acid salt, a phosphine oxide, and a phosphine, so as to obtain a flame retardant; or a monoalcohol containing from 12 to 16 carbon atoms or an amine selected from the group consisting of linear alkylamines, branched alkylamines, cycloalkylamines, alkoxyamines, amino alcohols, cyclic amines containing at least one nitrogen atom in a cyclic structure, an alkylenediamine, a polyetherdiamine, and a polyalkylenepolyamine, so as to obtain an auxiliary that is incorporated into the composition of detergents; or an alkylene oxide, a phenylene oxide or to a reaction with an alkylene oxide, a phenylene oxide and a glycidyl ether or to a homopolymerization reaction, so as to obtain an epichlorohydrin elastomer.

11. The product according to claim 2, comprising glycerol in a content greater than or equal to 500 g/kg of product.

12. A process for manufacturing dichloropropanol, in which the glycerol-containing product according to claim 2 is reacted with a chlorinating agent.

13. A process for manufacturing dichloropropanol, in which the glycerol-containing product according to claim 3 is reacted with a chlorinating agent.

14. A process for manufacturing dichloropropanol, in which the glycerol-containing product according to claim 11 is reacted with a chlorinating agent.

15. The process according to claim 13, wherein the dichloropropanol is subjected to a dehydrochlorination reaction in order to obtain epichlorohydrin.

16. The process according to claim 13, wherein the dichloropropanol is subjected to a dehydrochlorination reaction in order to obtain epichlorohydrin.

17. The process according to claim 14, wherein the dichloropropanol is subjected to a dehydrochlorination reaction in order to obtain epichlorohydrin.

18. The process according to claim 15, wherein the epichlorohydrin obtained is subjected to a reaction with:
at least one compound containing at least one active hydrogen atom, so as to obtain an epoxy derivative, selected from the group consisting of an epoxy resin, a glycidyl ether, a glycidyl ester, a glycidyl amide, a glycidyl imide, and a mixture of at least two of them; or
ammonia, an amine, a polyaminoamide or a polyimine, so as to obtain a coagulant; or
a polyamine, a polyamide or a polyaminoamide, so as to obtain a water-resistant resin for the treatment of paper; or
an amine or an amine salt, so as to obtain a cationizing agent; or
a compound selected from the group consisting of phosphoric acid, a phosphoric acid salt, a phosphorus oxychloride, a phosphoric acid ester, a phosphonic acid, a phosphonic acid ester, a phosphonic acid salt, a phosphinic acid, a phosphinic acid ester, a phosphinic acid salt, a phosphine oxide, and a phosphine, so as to obtain a flame retardant; or
a monoalcohol containing from 12 to 16 carbon atoms or an amine selected from the group consisting of linear alkylamines, branched alkylamines, cycloalkylamines, alkoxyamines, amino alcohols, cyclic amines containing at least one nitrogen atom in a cyclic structure, an alkylenediamine, a polyetherdiamine, and a polyalkylenepolyamine, so as to obtain an auxiliary that is incorporated into the composition of detergents; or
an alkylene oxide, a phenylene oxide or to a reaction with an alkylene oxide, a phenylene oxide and a glycidyl ether or to a homopolymerization reaction, so as to obtain an epichlorohydrin elastomer.

19. The process according to claim 16, in which the epichlorohydrin obtained is subjected to a reaction with:
at least one compound containing at least one active hydrogen atom, so as to obtain an epoxy derivative, selected from the group consisting of an epoxy resin, a glycidyl ether, a glycidyl ester, a glycidyl amide, a glycidyl imide or a mixture of at least two of them; or ammonia, an amine, a polyaminoamide or a polyimine, so as to obtain a coagulant; or
a polyamine, a polyamide or a polyaminoamide, so as to obtain a water-resistant resin for the treatment of paper; or
an amine or an amine salt, so as to obtain a cationizing agent; or
a compound selected from the group consisting of phosphoric acid, a phosphoric acid salt, a phosphorus oxychloride, a phosphoric acid ester, a phosphonic acid, a phosphonic acid ester, a phosphonic acid salt, a phosphinic acid, a phosphinic acid ester, a phosphinic acid salt, a phosphine oxide, and a phosphine, so as to obtain a flame retardant; or
a monoalcohol containing from 12 to 16 carbon atoms or an amine selected from the group consisting of linear alkylamines, branched alkylamines, cycloalkylamines, alkoxyamines, amino alcohols, cyclic amines containing at least one nitrogen atom in a cyclic structure, an alkylenediamine, a polyetherdiamine, and a polyalkylenepolyamine, so as to obtain an auxiliary that is incorporated into the composition of detergents; or
an alkylene oxide, a phenylene oxide or to a reaction with an alkylene oxide, a phenylene oxide and a glycidyl ether or to a homopolymerization reaction, so as to obtain an epichlorohydrin elastomer.

20. The process according to claim 17, in which the epichlorohydrin obtained is subjected to a reaction with:
at least one compound containing at least one active hydrogen atom, so as to obtain an epoxy derivative, selected from the group consisting of an epoxy resin, a glycidyl ether, a glycidyl ester, a glycidyl amide, a glycidyl imide and a mixture of at least two of them; or
ammonia, an amine, a polyaminoamide or a polyimine, so as to obtain a coagulant; or
a polyamine, a polyamide or a polyaminoamide, so as to obtain a water-resistant resin for the treatment of paper; or
an amine or an amine salt, so as to obtain a cationizing agent; or
a compound selected from the group consisting of phosphoric acid, a phosphoric acid salt, a phosphorus oxychloride, a phosphoric acid ester, a phosphonic acid, a phosphonic acid ester, a phosphonic acid salt, a phosphinic acid, a phosphinic acid ester, a phosphinic acid salt, a phosphine oxide, and a phosphine, so as to obtain a flame retardant; or
a monoalcohol containing from 12 to 16 carbon atoms or an amine selected from the group consisting of linear alkylamines, branched alkylamines, cycloalkylamines, alkoxyamines, amino alcohols, cyclic amines containing at least one nitrogen atom in a cyclic structure, an alkylenediamine, a polyetherdiamine, and a polyalkylenepolyamine, so as to obtain an auxiliary that is incorporated into the composition of detergents; or
an alkylene oxide, a phenylene oxide or to a reaction with an alkylene oxide, a phenylene oxide and a glycidyl ether or to a homopolymerization reaction, so as to obtain an epichlorohydrin elastomer.

* * * * *

UNITED STATES PATENT AND TRADEMARK OFFICE
CERTIFICATE OF CORRECTION

PATENT NO. : 8,314,205 B2
APPLICATION NO. : 12/745802
DATED : November 20, 2012
INVENTOR(S) : Patrick Gilbeau et al.

It is certified that error appears in the above-identified patent and that said Letters Patent is hereby corrected as shown below:

Column 12, Line 50, "The process according to claim 8" should read --The process according to claim 9--

Signed and Sealed this
Nineteenth Day of March, 2013

Teresa Stanek Rea
*Acting Director of the United States Patent and Trademark Office*